United States Patent [19]

Zimmermann et al.

[11] Patent Number: 5,352,684
[45] Date of Patent: Oct. 4, 1994

[54] PYRIDINES AS MEDICAMENTS

[75] Inventors: Peter Zimmermann; Wolf-Rüdiger Ulrich, both of Konstanz, Fed. Rep. of Germany

[73] Assignee: BYK Gulden Lomberg Chemische Fabrik GmbH, Konstanz, Fed. Rep. of Germany

[21] Appl. No.: 934,738

[22] PCT Filed: Apr. 8, 1991

[86] PCT No.: PCT/EP91/00661

§ 371 Date: Oct. 9, 1992

§ 102(e) Date: Oct. 9, 1992

[87] PCT Pub. No.: WO91/15484

PCT Pub. Date: Oct. 17, 1991

[30] Foreign Application Priority Data

Apr. 10, 1990 [CH] Switzerland ............ 01 222/90

[51] Int. Cl.$^5$ ............ A61K 31/44; A61K 31/445; C07D 401/06; C07D 401/12
[52] U.S. Cl. ............ 514/299; 514/314; 514/318; 514/343; 546/168; 546/183; 546/194; 546/281

[58] Field of Search ............ 546/156, 201, 281, 183, 546/168, 194, 281; 514/343, 314, 299, 318, 343

[56] References Cited

U.S. PATENT DOCUMENTS 4,707,486 11/1987 Flockerzi et al. ............ 514/318
4,975,440 12/1990 Flockerzi et al. ............ 514/318

FOREIGN PATENT DOCUMENTS 0285267 10/1988 European Pat. Off. .

OTHER PUBLICATIONS

Chemical Abstracts, Band 112, 1990 112:895.

*Primary Examiner*—Marianne M. Cintins
*Assistant Examiner*—Phyllis G. Spivack
*Attorney, Agent, or Firm*—Jacobson, Price, Holman & Stern

[57] ABSTRACT

Dihydropyridines of formula (I), in which the substituents and symbols have the meanings given in the description, are novel substances with interesting pharmacological properties. A method for their preparation and their uses are also presented.

8 Claims, No Drawings

PYRIDINES AS MEDICAMENTS

FIELD OF USE OF THE INVENTION

The invention relates to new pyridines, processes for their preparation, their use and medicaments containing them. The compounds according to the invention are employed in the pharmaceutical industry for the preparation of medicaments.

Known Technical Background

It is known that certain pyridines substituted in various ways have pharmacologically beneficial properties. European Patent Application EP-A-285 267 thus describes certain pyridines and dihydropyridines which are to be employed for the treatment and prevention of liver damage. Chemical Abstracts (Volume 112, 1990, page 5, Abstract 89s) references an article from the Journal of Chromatography (1989, 494, 209–17), in which the isolation of pyridine metabolites corresponding to manidipine is described. Surprisingly, it has now been found that the new compounds described below in more detail have particularly interesting pharmacological properties, by which they differ in an advantageous manner from the compounds of the prior art.

DESCRIPTION OF THE INVENTION

The invention relates to new pyridines of the formula I

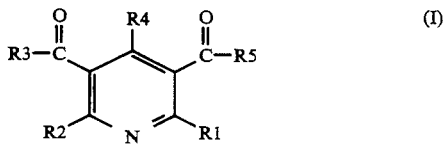

wherein
one of the radicals R1 and R5 denotes 1–6C-alkyl and the other denotes the grouping -E1-E2-N(R6a)R6b
R2 denotes hydrogen, 1–6C-alkyl or, together with R3, 2–3C-alkylene,
R3 denotes 1–4C-alkyl, 1–4C-alkoxy, 3–5C-alkoxyalkyl, 3–5C-alkoxyalkoxy or, together with R2, 2–3C-alkylene,
R4 denotes phenyl which is substituted by R41 and R42,
R41 denotes hydrogen, hydroxyl, halogen, nitro, cyano, trifluoromethyl, 1–4C-alkyl, 1–4C-alkoxy, 1–4C-alkoxy which is completely or partly substituted by fluorine, 1–4C-alkonycarbonyl, 2–5C-acyl, amino or mono-or di-1–4C-alkylamino,
R42 denotes hydrogen, hydroxyl, halogen, nitro, cyano, trifluoromethyl, 1–4—C-alkyl, 1–4C-alkoxy, 1–4C-alkoxy which is completely or partly substituted by fluorine, 1–4C-alkoxycarbonyl, 2–5C-acyl, amino or mono- or di-1–4C-alkylamino,
E1 denotes methylene ($CH_2$),
E2 straight-chain or branched 1–7C-alkylene, the grouping -($CH_2$)$_m$-E-($CH_2$)$_n$- or the grouping -A1-O-A2,
E denotes vinylene (—CH=CH—) or ethinylene (—CaC-),
m denotes the number 1 or 2,
n denotes the number 1 or 2,
A1 denotes a bond or 2–4C-alkylene,
A2 denotes 2–4C-alkylene or 2—C-alkylenoxy-2C-alkylene,
R6a and R6b, together and including the nitrogen atom to which they are both bonded, represent a radical of the formula

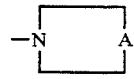

wherein
A denotes —$CH_2$—$CH_2$—C(R7)R8—$CH_2$—$CH_2$—, —$CH_2$—$CH_2$—CHR9—$CH_2$—$CH_2$—or —$CH_2$—$CH_2$—$CH_2$—CHR10-,
R7 denotes hydrogen (H) or aryl and
R8 denotes aryl, or
R7 and R8 together denote diarylmethylene,
R9 denotes diaryl-1–4C-alkyl and
R10 denotes aryl-1–4C-alkyl, wherein
aryl represents a ring of the formula

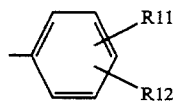

wherein R11 and R12 are identical or different and denote hydrogen (H), 1–4—C-alkyl, 1–4C-alkoxy, halogen, hydroxyl, trifluoromethyl or, together, methylenedioxy,
and the salts of these compounds.

1–6C-Alkyl is straight-chain or branched and denotes, for example, a hexyl, neopentyl, isopentryl, butyl, i-butyl, sec-butyl, t-butyl, propyl, isopropyl or, in particular, ethyl or methyl radical.

2–3C-Alkylene is ethylene or propylene, so that R2 and R3, if they have this meaning together, form, together with the carbonyl group, a 5- or 6-membered ring fused onto the dihydropyridine ring.

1–4C-Alkyl is straight-chain or branched and denotes, for example, a butyl, i-butyl, sec-butyl, t-butyl, propyl, isopropyl, ethyl or, in particular, methyl radical, 1–4C-Alkoxy contains, in addition to the oxygen atom, one of the above-mentioned 1–4C-alkyl radicals. Preferred 1–4C-alkoxy radicals R41, R42, R11 and R12 are the methoxy and the ethoxy radical. Preferred 1–4C-alkoxy radicals R3 are the isopropoxy and the t-butyoxy radical.

3–5C-Alkoxyalkyl represents, for example, a methoxyethyl, ethoxyethyl, propxyethyl or ethoxymethyl radical.

3–5C-Alkoxyalkyl represents, for example, a methoxyethoyl, ethoxyethoxy or propoxyethoxy radical.

Halogen is the context of the invention denotes bromine, fluorine and, in particular, chlorine.

1–4C-Alkoxy which is completely or partly substituted by fluorine is, for example, 1,1,2,2—tetrafluoroethoxy, trifluoromethoxy, 2,2,2—trifluoroethoxy or, in particular, difluoromethoxy.

2–5C-Acyl contains, in addition to the carbonyl group, one of the above-mentioned 1–4C-alkyl radicals. The acetyl radical is preferred. Mono- or di-1–4C-alkylamino contains, in addition to the nitrogen atom, one or two of the abovementioned 1–4C-alkyl radicals.

Di-1-4C-alkylamino is preferred, and here in particular dimethyl-, diethyl- or diisopropylamino.

Straight-chain or branched 1-7C-alkylene is, for example, methylene (—CH$_2$—), ethylene (—CH$_2$—CH$_2$—), trimethylene (—CH$_2$—CH$_2$—CH$_2$—), tetramethylene (—CH$_2$—CH$_2$—CH$_2$—CH$_2$—), 1,2—dimethylethylene [—CH(CH$_3$)—CH(CH$_3$)-], 1,1-dimethylethylene [—C(CH$_3$)$_2$—CH$_2$—], 1,1-dimethylpropylene [—C(CH$_3$)$_2$—CH$_2$—CH$_2$—9 , 2,2-dimethyl ethylene [—CH$_2$—C(CH$_3$)$_2$-], isopropylene [—C(CH$_3$)$_2$], 1-methylethylene [—CH(CH$_3$)CH$_2$-·, pentamethylene (—CH$_2$—CH$_2$—CH$_2$—CH$_2$—CH$_2$—) and hexamethylene (—CH$_2$—CH$_2$—CH$_2$—CH$_2$—CH$_2$—CH$_2$—).

2-4C-Alkylene represents ethylene (—CH$_2$—CH$_2$—, trimethylene (—CH$_2$—CH$_2$—CH$_2$—) and tetramethylene (—CH$_2$—CH$_2$—CH$_2$—CH$_2$), ethylene being preferred.

2C-Alkylenoxy-2C-alkylene represents ethylene which is substituted by ethylenoxy (—CH$_2$—CH$_2$—O—CH$_2$—).

Aryl represents phenyl which is substituted by R11 and R12. Examples of aryl radicals which may be mentioned are the radicals phenyl, 4-methoxyphenyl, 4-chlorophenyl, 4-methylphenyl, 4-fluorophenyl, 3-fluorophenyl, 3-chlorophenyl, 2—chlorophenyl, 3-methoxyphenyl, 2—methoxyphenyl, 2-ethoxyphenyl, 2-methylphenyl, 3-chloro-4-methylphenyl, 3,4-dichlorophenyl, 3,6-dichlorophenyl, 2,4-dimethylphenyl, 2,6-dimethylphenyl, 3,4-dimethylphenyl, 3,4-methylenedioxyphenyl, 2-trifluoromethylphenyl and 3-trifluoromethylphenyl.

Diaryl-1-4C-alkyl is 1-4C-alkyl which is substituted by two aryl radicals. Diaryl-1-4c-alkyl is, in particular, diphenylmethyl (benzhydryl) or substituted benzhydryl, such as e.g. 4,4'-difluorobenzyl, 4,4'-dimethylbenzhydryl, 4,4'-dimethylbenzhydryl or 4,4'-dichlorobenzhydryl.

Aryl-1-4l C-alkyl represents 1-4C-alkyl which is substituted by aryl. Examples of aryl-1-4C-alkyl radicals which may be mentioned are the radicals: 4-methylbenzyl, 4-methoxybenzyl, 4-chlorobenzyl, 1-phenethyl, 2-phenylethyl, 3-phenylpropyl, 3-chlorobenzyl, 2,5-dimethylbenzyl, 4-fluorobenzyl, 3-methylbenzyl and, in particular, benzyl.

Possible salts are all the salts with acids. The pharmacologically tolerated salts of the inorganic and organic which are customarily used in the pharmaceutical industry may be mentioned in particular. Salts which are not tolerated pharmacologically and which may initially be obtained as process products, for example, during preparation of the compounds according to the invention on an industrial scale are converted into pharmacologically tolerated salts by processes which are know to the expert. Suitable such salts are, for example, water-soluble and water-insoluble acid addition salts, such as the hydrochloride, hydrobromide, hydriodide, phosphate, nitrate, sulphate, acetate, citrate, gluconate, benzoate, bibenzate, fendizoate, butyrate, sulphosalicylate, maleate, laurate, malate, fumarate, succinate, oxalate, tartrate, amsonate, metembonate, stearate, tosylate, 2-hydroxy-3-naphthoate, 3-hydroxy-2-napthoate or mesylate.

One embodiment (embodiment a) of the invention comprises compounds of the formula Ia

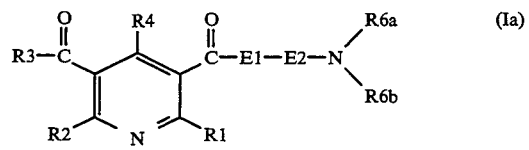

wherein
R1 denotes 1-6C-alkyl and R2, R3, R4, E1, E2, R6a and R6b have the abovementioned meanings, and the salts of these compounds.

A further embodiment (embodiment b) of the invention comprises compounds of the formula Ib

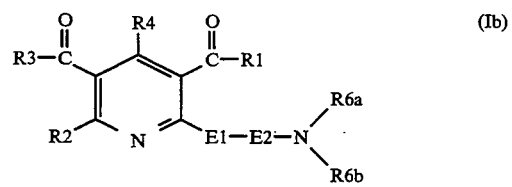

wherein
R1 denotes 1-6C-alkyl and R2, R3, R4, E1, E2, R6a and R6b have the abovementioned meanings, and the salts of these compounds.

Compounds which are to be singled out are those of the formula I in which one of the radicals R1 and R5 denotes 1-6C-alkyl and the other denotes the grouping -E1-E2—N(R6a )R6b, R2 denotes 1-4C-alkyl or, together with R3, 2-3c-alkylene.

R3 denotes 1-4C-alkyl, branched-chain 3-4C-alkoxy or, together with R2, 2-3C-alkylene, R4 denotes phenyl which is substituted by R41 and R42, R41 denotes hydrogen, chlorine or nitro, R42 denotes hydrogen or chlorine, E1 denotes methylene (CH$_2$), R2 denotes ethylene, propylene, tetramethylene, pentamethylene, hexamethylene or the grouping -A1O-A2, A1 denotes a bond, A2 denotes ethylene, R6a and R6b, together and including the nitrogen atom to which they are both bonded, represent a radical of the formula

wherein
A denotes —CH$_2$—CH$_2$—C(R7)R8—CH$_2$—CH$_2$-, —CH$_2$—CH$_2$—CHR9—CH$_2$—CH$_2$—or —CH$_2$—CH$_2$—CH$_2$—CHR10, R7 denotes hydrogen or phenyl and R8 denotes phenyl, or R7 and R8 together denote diphenylmethylene, R9 denotes diphenylmethyl (benzhydryl) and R10 denotes benzyl or 4-chlorobenzyl, and the salts of these compounds.

Compounds of embodiments a and b which are to be singled out are those of the formulae I and Ib in which R1 denotes 1-6C-alky and R2, R3R4, R41, R42, R1, E2, A1, A2R6a, R6b, A, R7, R8, R9 and R10 have the meanings given for the compounds which are to be singled out.

Preferred compounds of the formula I are those in which one of the radicals R1 and R5 denotes 1–4C-alkyl and the other denotes the grouping -E1-E2—N(-R6a)R6b, R2 denotes 1–4C-alkyl or, together with R3, 2–3C-alkylene,
R3 denotes 1–4C-alkyl, branched-chain 3–4C-alkoxy or, together with R2, 3–3—C-alkylene,
R4 denotes 3-nitrophenyl or 2,3-dichlorophenyl,
E1 denotes methylene,
E2 denotes propylene, tetramethylene, pentamethylene, hexamethylene or the grouping -A1-O-A2,
A1 denotes a bond,
A2 denotes ethylene,
R6a and R6b, together and including the nitrogen atom to which they are both bonded, represent a radical of the formula

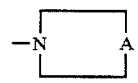

wherein
A denotes —CH$_2$—CH$_2$—C(R7)R8—CH$_2$—CH$_2$-,
R7 denotes phenyl and
R8 denotes phenyl, or
R7 and R8 together denote diphenylmethylene, and the salts of the these compounds, Preferred compounds of embodiments a and b are those of the formulae Ia and Ib in which R1 denotes 1–4C-alkyl and R2, R3, R4, E1, E2, A1, A2, R6a, R6b, A, R7 and R8 have the meanings given for the preferred compounds.

Examples of selected compounds of the formulae Ia and Ib according to the invention are shown in the following Table I with their particular substituent definitions.

TABLE I

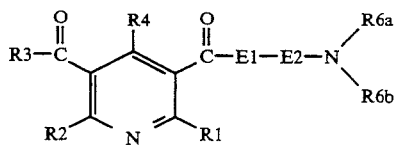

(Ia)                (Ib)

| R1 | R2 | R3 | R4 | —E1—E2— | —N(R6a)(R6b) |
|---|---|---|---|---|---|
| CH$_3$ | CH$_3$ | CH$_3$ | 3-NO$_2$-C$_6$H$_4$ | —CH$_2$—CH$_2$—CH$_2$—CH$_2$— | 4,4-diphenylpiperidin-1-yl |
| CH$_3$ | CH$_3$ | (CH$_3$)$_3$CO | 3-NO$_2$-C$_6$H$_4$ | —CH$_2$—CH$_2$—CH$_2$—CH$_2$— | 4,4-diphenylpiperidin-1-yl |
| CH$_3$ | CH$_3$ | CH$_3$ | 2,3-Cl$_2$-C$_6$H$_3$ | —CH$_2$—CH$_2$—CH$_2$—CH$_2$— | 4,4-diphenylpiperidin-1-yl |

TABLE I-continued

Structure (Ia): R3-C(=O)- at 5-position, R4 at 4-position, -C(=O)-E1-E2-N(R6a)(R6b) at 3-position, R2 at 6-position, R1 at 2-position of pyridine.

Structure (Ib): R3-C(=O)- at 5-position, R4 at 4-position, -C(=O)-R1 at 3-position, R2 at 6-position, -E1-E2-N(R6a)(R6b) at 2-position of pyridine.

| R1 | R2 | R3 | R4 | —E1—E2— | —N(R6a)(R6b) |
|---|---|---|---|---|---|
| CH₃ | CH₃ | CH₃ | 2-Cl-phenyl | —CH₂—CH₂—CH₂—CH₂— | 4,4-diphenylpiperidin-1-yl |
| CH₃ | CH₃ | CH₃ | 3-NO₂-phenyl | —CH₂—CH₂—CH₂— | 4,4-diphenylpiperidin-1-yl |
| CH₃ | CH₃ | CH₃ | 3-NO₂-phenyl | —CH₂—CH₂—CH₂—CH₂— | 4-(diphenylmethylene)piperidin-1-yl |
| CH₃ | CH₃ | (CH₃)₃CO | 3-NO₂-phenyl | —CH₂—CH₂—CH₂—CH₂— | 4-(diphenylmethylene)piperidin-1-yl |
| CH₃ | CH₃ | CH₃ | 3-NO₂-phenyl | —CH₂—CH₂—CH₂—CH₂— | 4-phenylpiperidin-1-yl |
| CH₃ | CH₃ | (CH₃)₃CO | 3-NO₂-phenyl | —CH₂—CH₂—CH₂—CH₂— | 4-phenylpiperidin-1-yl |

TABLE I-continued
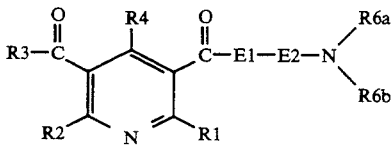
| R1 | R2 | R3 | R4 | —E1—E2— | —N(R6a)(R6b) |
|---|---|---|---|---|---|
| CH3 | CH3 | CH3 | 3-NO2-phenyl | —CH2—CH2—CH2—CH2— | N-piperidinyl-4-CH(phenyl)2 |
| CH3 | CH3 | (CH3)3CO | 3-NO2-phenyl | —CH2—CH2—CH2—CH2— | N-piperidinyl-4-CH(phenyl)2 |
| CH3 | CH3 | CH3 | 3-NO2-phenyl | —CH2—CH2—CH2—CH2— | N-pyrrolidinyl-2-CH2-phenyl |
| CH3 | CH3 | (CH3)3CO | 3-NO2-phenyl | —CH2—CH2—CH2—CH2— | N-pyrrolidinyl-2-CH2-phenyl |
| CH3 | CH3 | CH3 | 3-NO2-phenyl | —CH2—CH2—CH2—CH2— | N-pyrrolidinyl-2-CH2-(4-Cl-phenyl) |
| CH3 | CH3 | (CH3)3CO | 3-NO2-phenyl | —CH2—CH2—CH2—CH2— | N-pyrrolidinyl-2-CH2-(4-Cl-phenyl) |

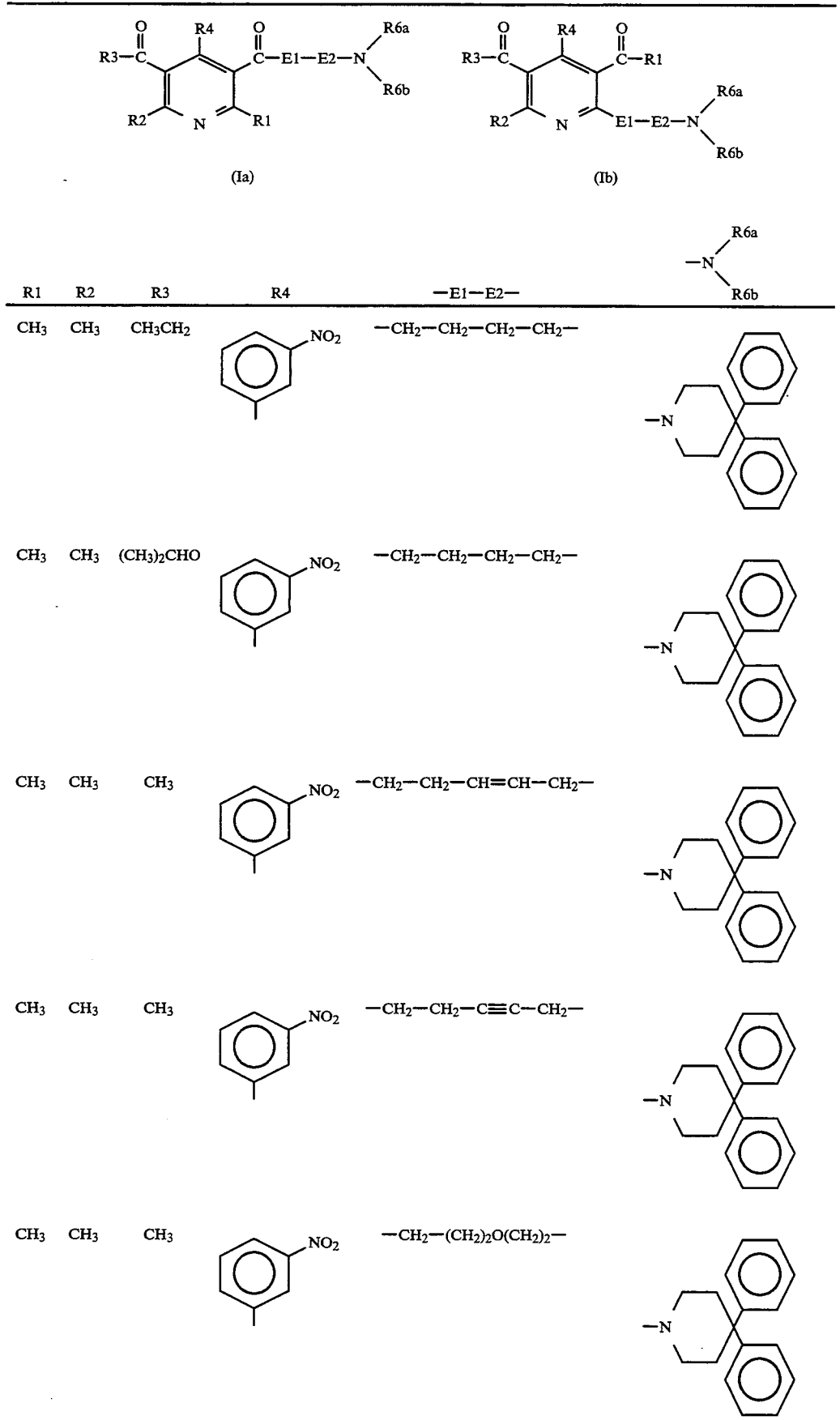

TABLE I-continued

Structure (Ia) and (Ib) shown with substituents R1, R2, R3, R4, E1–E2, and NR6aR6b.

| R1 | R2 | R3 | R4 | —E1—E2— | —N(R6a)(R6b) |
|---|---|---|---|---|---|
| CH3 | CH3 | (CH3)3CO | 3-nitrophenyl | —CH2—O—CH2—CH2— | 4,4-diphenylpiperidin-1-yl |
| CH3 | CH3 | (CH3)3CO | 3-nitrophenyl | —(CH2)5— | 4,4-diphenylpiperidin-1-yl |
| CH3 | CH3 | (CH3)3CO | 3-nitrophenyl | —(CH2)6— | 4,4-diphenylpiperidin-1-yl |
| CH3 | CH3 | (CH3)3CO | 3-nitrophenyl | —(CH2)7— | 4,4-diphenylpiperidin-1-yl |
| CH3 | CH3 | CH3 | 3-nitrophenyl | —CH2—O—CH2—CH2— | 4,4-diphenylpiperidin-1-yl |

TABLE I-continued
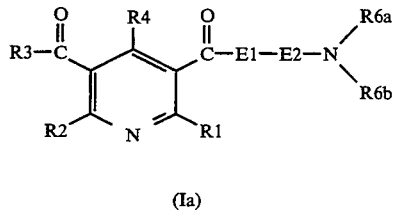
| R1 | R2 | R3 | R4 | —E1—E2— | —N(R6a)(R6b) |
|---|---|---|---|---|---|
| CH3 | CH3 | CH3 | 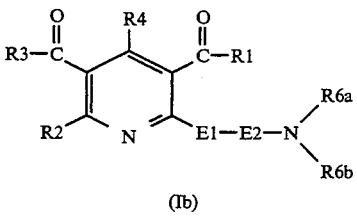 (3-NO2-phenyl) | —(CH2)5— | 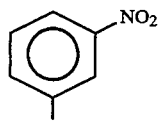 |
| CH3 | CH3 | CH3 | 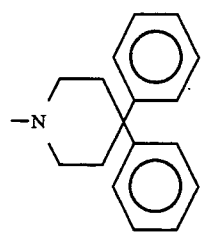 (3-NO2-phenyl) | —(CH2)6— | 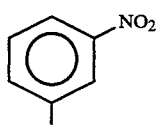 |
| CH3 | CH3 | CH3 | 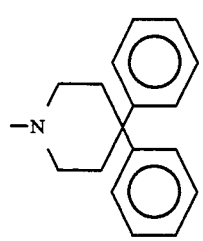 (3-NO2-phenyl) | —(CH2)7— | 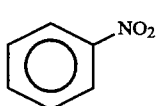 |
| CH3 | CH3 | CH3 | 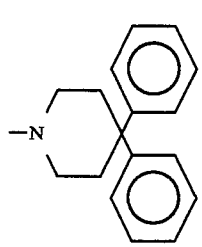 (2,3-diCl-phenyl) | —CH2—O—CH2—CH2— | 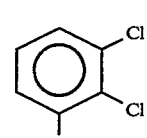 |
| CH3 | CH3 | CH3 | 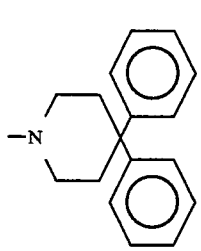 (2,3-diCl-phenyl) | —(CH2)5— | 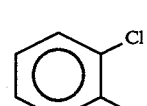 |

TABLE I-continued

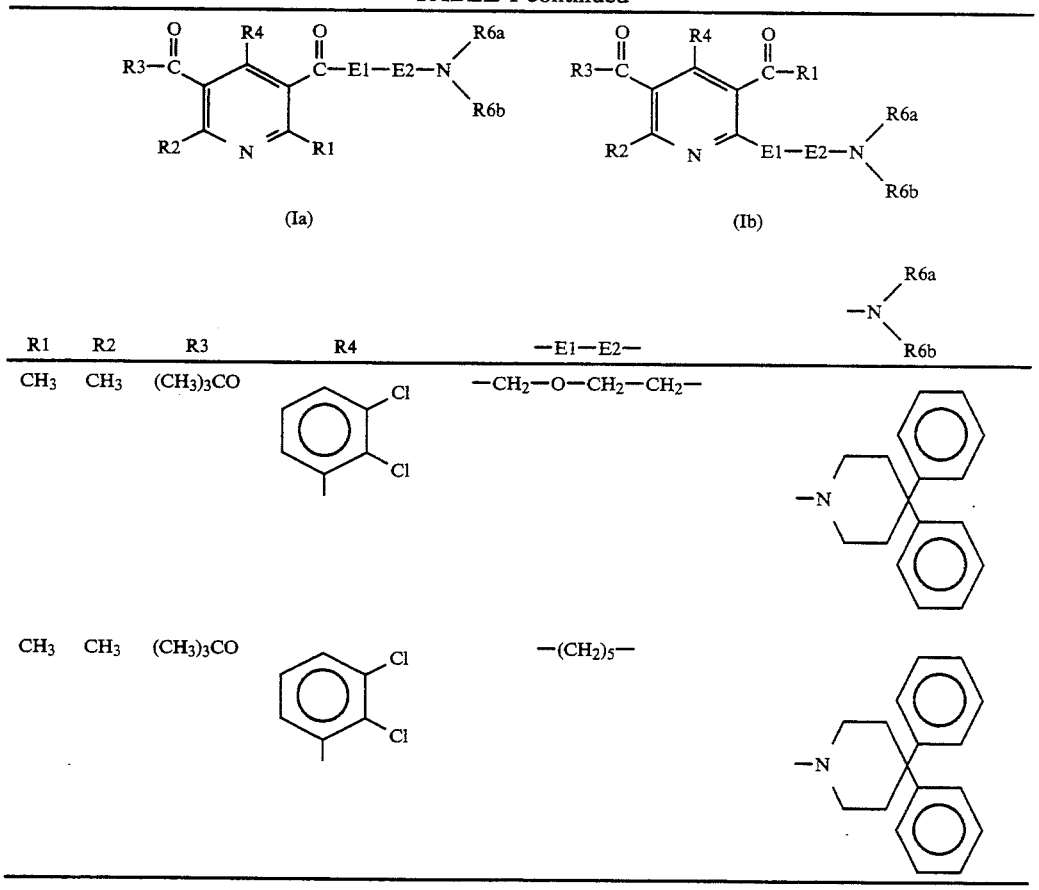

| R1 | R2 | R3 | R4 | —E1—E2— | —N(R6a)(R6b) |
|----|----|----|----|---------|--------------|
| CH3 | CH3 | (CH3)3CO | 2,3-dichlorophenyl | —CH2—O—CH2—CH2— | 4,4-diphenylpiperidin-1-yl |
| CH3 | CH3 | (CH3)3CO | 2,3-dichlorophenyl | —(CH2)5— | 4,4-diphenylpiperidin-1-yl |

The invention furthermore relates to a process for the preparation of the compounds of the formula I and their salts. The process if characterized in that compounds of the formula II

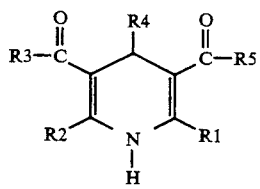

are oxidized, and subsequently, if desired, resulting free compounds are converted into their salts or resulting salts are converted into the free compounds, wherein R1, R2, R4 and R5 have the abovementioned meanings.

The oxidation is carried out in a manner familiar to the expert, in inert solvents, such as, for example, methylene chloride, at temperatures of between 0° and 200° C., preferably between 0° and 50° C.

Inorganic and organic oxidizing agents, such as, for example, manganese dioxide, nitric acid, chromium(VI) oxide or alkali metal dichromate, nitrogen oxides, chloranil or tetracyanobenzoquinone, or anodic oxidation in the presence of a suitable electrolyte system are suitable for the oxidation (dehydrogenation).

The dihydropyridines of the formula II are new and the invention likewise relates to them. They can be prepared e.g. by processes analogous to those described in the patent applications EP-A-176 956, EP-A-138 505, EP-A-242 829, EP-A-314 038 or DE-OS 36 27 742, but preferably in accordance with the following equation

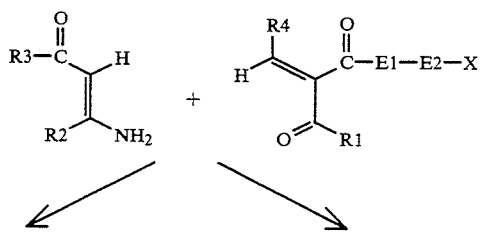

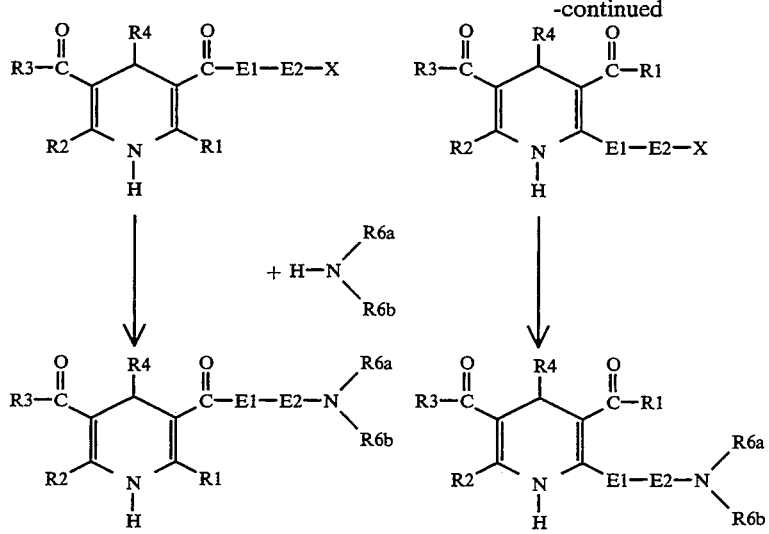

wherein R1 denotes 1-6C-alkyl, X represents a leaving group (preferably a halogen atom, in particular bromine or chlorine) and R2, R3, R4E1, E2, R67a and R6b have the abovementioned meanings.

The following examples illustrate the invention in more detail without limiting it. The invention preferably relates to the compounds of the general formula I mentioned by name in the examples and the salts of these compounds. M.p. denotes melting point, the abbreviating h is used for hour(s) and the abbreviation min is used for minutes. Decomp. represents decomposition. "Ether" is understood as meaning diethyl ether.

EXAMPLES

End Products 1. 5-Acetyl-2,6-dimethyl-3-[5-(4,4-diphenyl-1-piperdinyl)pentanoyl]-4-(3-nitrophenyl)-pyridine fumarate 1.2 g (1.9 mmol) 5-acetyl-1,4-dihydro-2,6-dimethyl-3-[5-(4,4-diphenyl-1-piperidinyl)pentanoyl]-4-(3-nitrophenyl)-pyridine hydrochloride are converted into the free base by shaking with excess 1N NaOH, and the base is extracted with ethyl acetate. The organic phase is dried over magnesium sulphate, filtered and concentrated. The residue is dried in vacuo and is then taken up in 30 ml anhydrous methylene chloride. 2.5 g(29 mmol) manganese dioxide are added. The mixture is stirred vigorously at room temperature for 12 h. Another 2 g (23 mmol) manganese dioxide are added in portions of 0.5 g each in the course of a further 8 h. The mixture is then centrifuged and the sediment is decanted off. The supernatant is concentrated and the residue is chromatographed over silica gel with toluene/acetone=8/2. The product thus obtained is taken up in 30 ml isopropanol, and 0.22 g (1.9 mmol) fumaric acid in 20 ml isopropanol is added. The title compound crystallized overnight. Yield: 0.7 g (52%). M.p.: 181°-190° C. decomp. (acetonitrile).

2. 3,5-Diacetyl-2—[4-(4,4-diphenyl-1-piperidinyl)-butyl]-6-methyl-4-(3-nitrophenyl)-pyridine fumarate 2.4 g (3.8 mmol) 3,5-diacetyl-1,4-dihydro-2-[4-(4,4-diphenyl-1-piperidinyl)butyl]-6-methyl-4-(3-nitrophenyl)-pyridine hydrochloride are first converted into the free base, which is then oxidized to the pryidine with 9 g (0.1 mol) manganese dioxide, as described in Example 1. Working up is carried out as described in Example 1. Chromatography gives 1.5 g product, which are taken up in 30 ml isopropanol, and 0.3 g (2.6 mmol) fumaric acid in 30 ml isopropanol is added. The product obtained in this manner is taken up in 25 ml acetonitrile, and 25 ml diisopropyl ether are added under the influence of heat. The title compound crystallizes overnight. Yield: 0.9 g (33%). M.p.: 178°-181° C. (acetonitrile/diisopropyl ether).

3. 3-Acetylene-2-[4-(4,4-diphenyl-1-piperidinyl)butyl]-5-tert-butoxycarbonyl-6-methyl-4-3-nitrophenyl)-pyridine fumarate 3 g (4.4. mmol) 3-acetyl-1,4-dihydro-2-[4-(4,4-diphenyl-1-piperidinyl)butyl]-5-tert-butoxycarbonyl-6-methyl-4-(3-nitrophenyl)-pyridine hydrochloride are oxidized to the pyridine with 12 g (0.14 mol) manganese dioxide as described in Example 1. The crude product is chromatographed with toluene/acetone=6/4. The product obtained in this manner is taken up in 10 ml isopropanol. The title compound crystallizes out after addition of 0.41 g (3.5 mmol) fumaric acid in 25 ml isopropanol. Yield: 2.15 g (64%). M.p.: 184°-186° C. decomp. (isopropanol).

4. (5-Acetyl-4-(2,3-dichlorophenyl)2,6-dimethyl-3-[5-(4,4-diphenyl-1-piperidinyl) pentanoyl]-pyridine fumarate 1.1 g (1.7 mmol) 5-acetyl-4-(2,3-dichlorophenyl)-1,4-dihydro-2,6-dimethyl-3-[5-(4,4-diphenyl-1-piperidinyl)-pentanoyl]-pyridine hydrochloride are first converted into the free base, which is then oxidized to the pyridine with 4.4 g (50 mmol) manganese dioxide, as described in Example 1. Working up is carried out as described in Example 1. The crude product is chromatographed over silica gel with toluene/acetone=6/4. 0.71 g of a yellow oil is obtained, which is taken up in 3.5 ml isopropanol, and 0.13 g (1.1 mmol) fumaric acid in 6 ml isopropanol is added. The title compound crystallizes overnight. Yield: 0.69 g (55%). M.p. 172°-173° C. decomp. (acetonitrile).

5. 5-Acetyl-2,6-dimethyl3-[6-(4,4-diphenyl)-1-piperidinyl)hexanoyl)]4,-(3-nitrophenyl)-pyridine fumarate 3 g (4.9 mmol) 5-acetyl-1,4-dihydro-2,6-dimethyl-3-[6-(4,4-diphenyl-1-piperidinyl)hexanoyl]-4-(3-nitrophenyl)-pyridine hydrochloride are first converted into the free base, which is then oxidized to the pyridine with 4 g out as described in Example 1. The crude product is chromatographed over silica gel with toluene/acetone=8/2. 1.9 g of a yellow oil are obtained, which are taken up in 10 ml isopropanol, and 0.36 g (3.1 mmol) fumaric acid in 10 ml isopropanol is added. The title compound crystallizes overnight. Yield: 1.6 g (45%). M.p. 169°–171° C. decomp.(isopropanol).

6. 3-Acetyl-5-tert-butoxycarbonyl-2-[4(4,4-diphenyl-1-piperidinyl)butyl]-4-(2,3-dichlorophenyl)-6-methyl-pyridine fumarate 1.5 g (2.1 mmol) 3-acetyl-5-tert-butoxycarbonyl-1,4-dihydro-4-(2,3-dichlorphenyl) 2-[4-(4,4-diphenyl-1-piperidinyl)butyl]-b 6-methyl-pyridine hydrochloride are first converted into the free base, which is then oxidized to the pyridine with 2 g (23 mmol) manganese dioxide, as described in Example 1. Working up is carried out as described in Example 1. The crude product is chromatographed over silica gel with toluene/acetone=9/1. 0.8 g of a yellow oil is obtained, which is taken up in 2 mol isopropanol, 0.14 g (1.2 mmol) fumaric acid in 10 ml isopropanol is added. The title compound crystallizes overnight. Yield: 0.75 g (45%). M.p. 189°–190° C. decomp. (acetonitrile).

7. 3,5-Diacetyl-2]6-(4,4-diphenyl-1-piperidinyl)hexyl]-6-methyl-4-(3-nitrophenyl) -pyridine fumarate 2 g(3 mmol) 3,5-diacetyl-1,4-dihydro-2-(1,4-dihydro-2-[6-(4,4-diphenyl-1-piperidinyl)hexyl]-6-methyl-4-(3-nitrophenyl)-pyridine hydrochloride are first converted into the free base, which is then oxidized to the pryidine with 4 g (46 mmol) manganese dioxide, as described in Example 1. Working up is carried out as described in Example 1. The crude product is chromatographed over silica gel with toluene/acetone=8/2. 0.5 g of a yellow oil is obtained, which is taken up 10 ml isopropanol, and 0.1 g (0.8 mmol) fumaric acid in 10 ml isopropanol is added. The title compound crystallizes overnight. Yield: 0.3 g (13%). M.p. 133°–138° C. (acetonitrile).

8. 5-Acetyl-2,6-dimethyl-3-[8-(4,4-diphenyl-1-piperidinyl)octanoyl]-4-(3-nitrophenyl)-pyridine fumarate 1 g (1.6mmol) 5-acetyl-1,4-dihydro-2,6-dimethyl-3,-[8-(4,4-diphenyl-1-piperidinyl) octanoyl]-4-(3-nitrophenyl)-pyridine is dissolved in 20 ml acetone, and 1.7 g (3.1 mmol) ammonium cerium(IV) nitrate in 20 ml water are added. After acetate. The organic phase is dried over magnesium sulphate, filtered and concentrated. 1 g of a solidified foam is obtained, which is dissolved in 5 ml isopropanol, while heating, and 0.18 g (1.6 mmol) fumaric acid in 10 ml isopropanol is added. The title compound crystallizes on cooling. Yield 0.93 g (78%). M.p. 159°–163° C. (acetonitrile).

9. 3-Acetyl-5-tert-butoxycarbonyl-2-[2-(4,4-diphenyl-1-piperidinyl)-1-ethoxymethyl -6-methyl-4-(3-nitrophenyl)-pyridine 2.5 g (3.6 mmol) 3-acetyl-5-tert-butoxycarbonyl-1,4-dihydro-2,-[2-(4,4-diphenyl -1-piperidinyl)-1-ethoxy)-methyl-4-(3-nitrophenyl)-pyridine hydrochloride are first converted into the free base as described in Example 1, and the base is then oxidized to the pyridine with 4 g (7.3 mmol) ammonium cerium(IV) nitrate as described in Example 8. The crude product is chromatographed over silica gel with toluene/acetone=1/1. The title compound thus obtained is recrystallized from 20 ml methanol. Yield: 1.5 g (60%). M.p. 140–141° C. (methanol).

10. 3-[6(4,4-Diphenyl-1-piperidinyl)hexanoyl]-2-methyl-4-(3-nitrophenyl)-5-oxo-5,6,7,8-tetrahydro-quinoline fumarate 2.3 g (3.7 mmol) 3-[6-(4,4-diphenyl-1,-piperidinyl)-hexaonyl]-1,4,5,6,7,8-hexahydro-2-methyl-4-(3-nitrophenyl)-5-oxo-quinoline are dissolved in 20 ml acetone, and 4 g (7.4 mmol) ammonium cerium(IV) nitrate in 20 ml water are added. After 15 min, 50 ml water are added. The mixture is extracted with ethyl acetate. The organic phase is washed neutral with aqueous sodium bicarbonate solution, dried over magnesium sulphate, filtered and concentrated. The residue is taken up in 50 ml isopropanol, and 0.43 g (3.7 mmol) fumaric acid in 50 ml isopropanol is added. The title compound crystallizes overnight. Yield: 1.75 g (65%). M.p. 235°237.5° C. decomp. (acetonitrile/methanol).

11. 5-Acetyl-2,6-dimethyl-3-[5–4-diphenylmethylene-1-piperidinyl)pentanoyl]4-(3-nitrophenyl)-pyridine fumarate 0.9 g (1.5 mmol) 5-acetyl-1,4-dihydro-2,6-dimethyl-3-[5-(4-diphenylmethylene-1-piperidinyl)pentanoyl]-4-(3-nitrophenyl)-pyridine is dissolved in 30 ml acetone, and 1.8 g (3.2 mmol) ammonium cerium(IV) nitrate in 20 ml water are added. After 15 min, 100 ml water are added. The mixture is extracted with ethyl acetate. The organic phase is washed neutral with aqueous sodium bicarbonate solution, dried over magnesium sulphate, filtered and concentrated. The residue is chromatographed with toluene/acetone=8/2. 0.73 g of a yellow oil is obtained, 5 ml is isopropanol is added. The title compound crystallizes when the mixture is left to stand. Yield: 0.7 g (65%). M.p. 197°–198° C. decomp. (isopropanol).

Starting compounds

A. 5-Acetyl-1,4-dihydro-2,6-dimethyl-3-(chloropentanoyl)4-(3-nitrophenyl)-pyridine and 3.5-diacetyl-1,4-dihydro-2-(4-chlorobutyl)-6-methyl-4-(3-nitrophenyl)-pyridine 32 g (0.103 mol) 1-chloro-6-(3-nitrophenylmethylene)-5,7-octanedione and 31 g (0.312 mol) 2-amino-2-penten-4-one are boiled under reflux in 250 ml methanol for 24 h. The mixture is concentrated and the residue is chromatographed over silica gel with ethyl acetate/petroleum ether =4/6. Yield: 32 g (79%). The product mixture contains the title compounds in a ratio of about 3/1. Title compound 1 partly crystallizes out when the mixture is left to stand. M.p.: 131°–132° C. (acetonitrile). Title compound 2, which remains as an oil, can be subsequently reacted directly without further purification.

B. 5-Acetyl-1,4-dihydro-2,6-dimethyl-4-(3-nitrophenyl)-3-[5-(4,4-diphenyl-1-piperidinyl)pentanoyl]-pyridine hydrochloride 5.5 g (14 mmol) 5-acetyl-1,4-dihydro-2,6-dimethyl-3-(5-chloropentanoyl)-4-(3-nitrophenyl)-pyridine and 4.2 g (28 mmol) sodium iodide are boiled under reflux in 200 ml anhydrous acetone for 24 h. The mixture is filtered and concentrated. The residue is boiled under reflux together with 8 g (28 mmol) 4,4-diphenylpiperidine hydrochloride and 8 g (58 mmol) potassium carbonate in 100 ml dioxane for 24 h. The mixture is filtered and concentrated, and the residue is chromatographed over silica gel with toluene/acetone=2/8. The product thus obtained is taken up in 120 ml isopropanol and the mixture is diluted with 150 ml diethyl ether. The title compound is precipitated by addition of ethereal hydrochloric acid . Yield: 4.75 g (54%). M.p.: 164°–167° C. (acetonitrile).

c. 3,5-Diacetyl-1,4-dihydro-2-[4-(4,4-diphenyl-1-piperidinyl)butyl-6-methyl-4-(3-nitrophenyl)-pyridine hydrochloride 5.5 g (14 mmol) 3,5-diacetyl-1,4-dihydro-2-(4-chlorobutyl)-6-methyl-4-(3-nitrophenyl)-pyridine and 4.2 g (28 mmol) sodium iodide are boiled under reflux in 200 ml anhydrous acetone for 24 h. The mixture is filtered and concentrated. The residue is boiled under reflux together with 8 g (28 mmol) 4,4-diphenylpiperidine hydrochloride and 8 g (58 mmol) potassium carbonate in 100 ml dioxane for 24 h. The mixture is filtered and concentrated, and the residue is chromatographed over silica gel with toluene/acetone=2/8. The product thus obtained is taken up in 120 ml isopropanol and the mixture is diluted with 150 ml diethyl ether. The title compound is precipitated by addition of ethereal hydrochloric acid. Yield: 4.6 g (52%). M.p: 225°–227° C. (acetonitrile).

D. 3-Acetyl-5-tert-butoxycarbonyl-2-(4-chlorobutyl)-1,4-dihydro-6-methyl-4-(3-nitrophenyl)-pyridine 24 g (79 mmol) 1-chloro-6-(3-nitrophenylmethylene)-5,7-octanedione and 25 g (0.159 mol) tert-butyl β-amino-crotonate are boiled under reflux in 200 ml 1-butanol for 18 h. The mixture is filtered and concentrated, and the residue is chromatographed over silica gel with toluene/acetone=9/1. The title compound is obtained as a yellow oil. Yield: 19.7 g (57%).

E. 3-Acetyl-1,4-dihydro-2-([4-(4,4-diphenyl-1-piperidinyl)butyl]-5-tert-butoxycarbonyl-6methyl-4-(3-nitrophenyl)-pyridine hydrochloride 7.6 g (17 mmol) 3-acetyl-5-tert-butoxycarbonyl-2-(4-chlorobutyl)-1,4-dihydro-6-methyl-4-(3-nitrophenyl)-pyridine are converted into the iodide with 5.2 g (35 mmol) sodium iodide in 300 ml anhydrous acetone as described in Example B. The iodide is then reacted with 7.7 g (26 mmol) diphenylpiperidine hydrochloride and 7.2 g (52 mmol) potassium carbonate in 100 ml dioxane as described in Example B. The crude product is chromatographed over silica gel with toluene/acetone=6/4. The product thus obtained is taken up in 30 ml acetonitrile. The title compound is precipitated by addition of ethereal hydrochloric acid. Yield: 3.7 g (32%). M.p.: 230≧-231° C. decomp. (acetonitrile).

F. 5-Acetyl-4-(2,3-dichlorophenyl)-1,4-dihydro-2,6-dimethyl-3-[5-(4,4-diphenyl-1-piperidinyl)pentanoyl]-pyridine hydrochloride 5 g (12 mmol) 5-acetyl-4-(2,3-dichlorophenyl)-1,4-dihydro-2,6-dimethyl-2,6-dimethyl-3-(5-chloropentanoyl)-pyridine are reacted first with 3.6 g (24 mmol) sodium iodide and then with 6.9 g (24 mmol) 4,4-diphenylpiperidine hydrochloride, as described for starting compound B. Working up is carried out as described for starting compound B. The crude product is chromatographed with toluene/acetone=7/3. The product thus obtained is taken up in 20 ml isopropanol and the mixture is diluted with 5 ml diethyl ether. The title compound is precipitated by addition of ethereal hydrochloric acid. Yield: 2.3 g (30%). M.p. 258°–259° C. decomp. (acetonitrile).

G. 5-Acetyl-4-(2,3-dichlorophenyl)-1,4-dihydro-2,6-dimethyl-3-(5-chloropentanoyl)-pyridine 10 g (30 mmol) 6-(2,3-dichlorophenyl-methylene)-1-5,7-octanedione and 6 g (60 mmol) 2-amino-2-penten-4-one are boiled under reflux in 100 ml 1-butanol for 7 h. The mixture is concentrated and the residue is chromatographed over silica gel with ethyl acetate-petroleum ether=3/7. The title compound is obtained as a yellow oil. Yield: 5.8 g (47%).

H. 5-Acetyl-1,4-dihydro-2,6-dimethyl-3-(6-bromohexanoyl)-4-(3-nitrophenyl)-pyridine 42 g (0.11 mol) 1-bromo-7-(3-nitrophenylmethylene)-6,8-nonanedione and 22 g (0.22 mmol) 2-amino-2-penten-4-one are boiled under reflux in 270 ml methanol for 20 h. The mixture is concentrated and the residue is chromatographed over silica gel with toluene/acetone=95/5. The title compound is obtained as a yellow oil. Yield: 22 g (44%).

I. 5-Acetyl-1,4-dihydro-2,6-dimethyl-3-[6-(4,4-diphenyl-1-piperidinyl)hexanoyl]-4-(3-nitrophenyl)-pyridine hydrochloride 9 g (20 mmol) 5-acetyl-1,4-dihydro-2,6-dimethyl-3-(6-bromohexanoyl)4-(3-nitrophenyl)-pyridine are reacted first with 6 g (40 mmol) sodium iodide, as described for starting compound B, and then with 11 g (38 mmol) 4,4-diphenylpiperidine hydrochloride. Working up is carried out as described for starting compound B. The crude product is chromatographed with toluene/acetone=1/1. The product thus obtained is taken up in 20 ml acetonitrile. The title compound is precipitated by addition of ethereal hydrochloric acid. Yield: 4 g (31%). M.p. 136° C. decomp. (acetonitrile).

K. 3-Acetyl-5-tert-butoxycarbonyl-1,4-dihydro-4-(2,3-dichlorophenyl)-2-(4-chlorobutyl)-6-methyl-pyridine 25 g (70 mmol) 6-(2,3-dichlorophenyl-methylene)-1-chloro-5,7-octanedione and 22 g (0.14 mol) tert-butyl β-amino-crotonate are boiled under reflux in 200 ml 1-butanol for 6 h. The mixture is concentrated and the residue is prepurified by chromatography with toluene/acetone=8/2. The product thus obtained is chromatographed again over silica gel with toluene/acetone=99/1. The title compound is obtained as a yellow oil. Yield: 5.8 g (18%).

L. 3-Acetyl-5-tert-butoxycarbonyl-1,4-dihydro-2[4-(4,4-diphenyl-1-piperidinyl)butyl]-4(2,3-dichlorophenyl)-6-methyl-pyridine hydrochloride 5.6 g (12.2 mmol) 3-acetyl-5-tert-butoxycarbonyl-1,4-dihydro-4-(2,3-dichlorophenyl)-2-(4-chlorobutyl)-6-methyl-pyridine are reacted first with 3.6 g (24.4 mmol) sodium iodide, as described for starting compound B, and then with 6 g (21 mmol) 4,4-diphenylpiperidine hydrochloride. Working up is carried out as described for starting compound B. The crude product is chromatographed with toluene/acetone=8/2. The product thus obtained is taken up in 30 ml isopropanol. The title compound is precipitated by addition of ethereal hydrochloric acid. Yield: 5.2 g (60%). M.p. 154°–156° C. decomp. (acetonitrile).

M. 3,5-Diacetyl-1,4-dihydro-2-(6-bromohexyl)-6-methyl-4-(3-nitrophenyl)-pyridine 45 g (0.14 mol) 1-bromo-8-(3-nitrophenylmethylene)-7,9-decanedione and 28 g (0.28 mol) 2-amino-2-penten-4-one are boiled under reflux in 300 ml methanol for 24 h. The mixture is concentrated and the residue is prepurified by chromatography with toluene/acetone=99/1. The product thus obtained is chromatographed again over silica gel with toluene-/ethyl acetate=8/2The title compound is obtained as a yellow oil. Yield: 10.3 g (16%).

N. 3,5-Diacetyl-1,4-dihydro-2-[6-(4,4-diphenyl-1-piperidinyl)hexyl]-6-methyl-4-(3-nitrophenyl)-pyridine hydrochloride 3.5 g (7.8 mmol) 3,5-diacetyl-1,4-dihydro-2-(6-bromohexyl)6-methyl-4-(3-nitrophenyl)-pyridine are reacted first with 2.3 g (15.6 mmol) sodium iodide, as described for starting compound B, and then with 4.3 g (15.6 mmol)4,4-diphenylpiperidine hydrochloride. Working up is carried out as described for starting compound B. The crude product is chromatographed with toluene/acetone=8/2. The product thus obtained is taken up in 5 ml acetonitrile and the mixture is diluted with 5 ml diethyl ether. The title compound is precipitated by addition of ethereal hydrochloric acid. Yield: 3 g (61%). M.p. 166°–167° C. (acetonitrile).

O. 5-Acetyl-3-(8-bromo-octanoyl)-1,4-dihydro-2,6-dimethyl-4-(3-nitrophenyl)-pyridine 35 g (91 mmol) 1-bromo-9-(3-nitrophenyl-methylene)-8,10-undercanedione and 18 g (0.18 mol) 2-amino-2-penten-4-one are boilder under reflux in 250 ml methanol for 42 h. The mixture is concentrated and the residue is chromatographed with toluene/ethyl acetate=8/2. The title compound is obtained as a yellow oil. Yield: 11.4 g (26%).

P. 5-Acetyl-1,4-dihydro-2,6-dimethyl-3-[8-(4,4-diphenyl-1-piperidinyl) octanoyl]-4-(3-nitrophenyl)-pyridine 10 g (21 mmol) 5-acetyl-3-(8-bromo-octanoyl)-1,4-dihydro-2,6-dimethyl-4(3-nitrophenyl)-pyridine are reacted first with 6.3 g (42 mmol) sodium iodide and then with 11. 5 g (40 mmol) 4,4-diphenylpiperidine hydrochloride, as described for starting compound B. Working up is carried out as described for starting compound B. The crude product is chromatographed with increasing polarity, first with toluene/acetone=9/1 and finally with toluene/acetone =6/4. The product thus obtained is recrystallized from 70 ml acetonitrile. The title compound is obtained as a yellow solid. Yield: 11 g (82%). M.p. 141°–145° C. (acetonitrile).

Q. 3-Acetyl-5-tert-butyloxycarbonyl-2-(2-chloro-1-ethoxy)methyl-1,4-dihydro -6-methyl-4-(3-nitrophenyl)-pyridine 13 g (40 mmol) 1-(2-chloro-1-ethyl)-3-(3nitrophenyl-methylene)-2,4-pentanedione and 12.8 g (80 mmol) tert-butyl β-amino-crononate are boiled under reflux in 100 ml 1-butanol for 5 h. The mixture is concentrated and the residue is chromatographed with toluene/acetone=95/5. The title compound is obtained as a yellow oil. Yield: 8.5 g (47%).

R. 3-Acetyl-5-tert-butoxycarbonyl-1,4-dihydro-2-[2-(4,4-diphenyl-1-piperidinyl) -1-ethoxy]methyl-6-methyl-4-(3-nitrophenyl)-pyridine hydrochloride 8.5 g (19 mmol) 3-acetyl-5-tert-butoxycarbonyl-2-(2-chloro-1-ethoxy)methoxy-1,4-dihydro-6-methyl-4-(3-nitrophenyl)-pyridine are reacted first with 5.6 g (38 mmol) sodium iodide, as described for starting compound B, and then with 10.3 g (36 mmol) 4,4-diphenylpiperidine hydrochloride. Working up is carried out as described for starting compound B. The crude product is chromatographed with toluene/acetone=9/1. The product thus obtained is taken up in 50 ml diethyl ether. The title compound is precipitated by addition of ethereal hydrochloric acid. Yield: 11 g (84%). M.p. 175°–177° C. (diethyl ether).

S. 3-(6—Chlorohexanoyl)-1,4,5,6,7,8-hexahydro-2-methyl-4-(3-nitrophenyl)-5-oxo-quinoline 37 g (0.33 mol) 3-aminocyclohex-2-en-1-one and 42 g (0.13 mol) 1-chloro-7-(3-nitrophenyl-methylene)-nonane-6,8-dione are boiled under reflux in 400 ml methanol for 38 h. The mixture is concentrated and the residue is chromatographed with toluene/acetone=8/2. The title compound is obtained as a yellow oil. Yield: 18 g (34%).

T. 3-[6-(4,4-diphenyl-1-piperidinyl)hexanoyl]1,4,5,6,7,8-hexahydro-2-methyl-4-(3-nitrophenyl)5-oxo-quinoline 6.6 g (16 mmol) 3-(6-chlorohexanoyl)-1,4,5,6,7,8,-hexahydro-2-methyl-4-(3-nitrophenyl) 5-oxo-quinoline and 9 g( 32 mmol) 4,4-diphenylpiperidine hydrochloride are boiled under reflux with 2.5 g (16 mmol) sodium iodide and 7 g (66 mmol) sodium carbonate in 150 ml acetone for 6 days. The mixture is filtered and concentrated, and the residue is taken up in 150 ml ethyl acetate. The mixture is extracted by shaking with 40 ml sodium thiosulphate solution (5%). The organic phase is dried over magnesium sulphate, filtered and concentrated. The residue is chromatographed over silica gel with toluene/acetone=8/2. The title compound is obtained as a yellow oil. Yield: 8 g (82%).

U. 5-Acetyl-1,4-dihydro-2,6-dimethyl-3-[5-(4-diphenylmethylene-1-piperidinyl)-pentanoyl]-4-(3-nitrophenyl)-pyridine 4.7 g (12 mmol) 5-acetyl-1,4-dihydro-2,6-dimethyl-3-(5-chloropentanoyl)-4-(3-nitrophenyl)-pyridine and 3 g (14 mmol) 4-diphenylmethylenepiperidine are boiled under reflux with 1.9 g (12 mmol) sodium iodide and 5 g (48 mmol) sodium carbonate in 200 ml acetone for 5 days. The mixture is filtered and concentrated, and the residue is taken up in 100 ml ethyl acetate. This solution is extracted by shaking with 40 ml sodium thiosulphate solution (5%). The organic phase is dried over magnesium sulphate, filtered and concentrated. The residue is chromatographed with toluene/acetone=6/4, The title compound is obtained as a yellow oil. Yield: 2.2 g (32%).

Commercial Usefulness

The compounds of the formula I and their salts have useful properties which render them commercially usable. They are primarily antineoplastic agents having an interesting cytostatic activity. They can be employed in the treatment of tumour diseases, for example for reducing or preventing the formation of metastases and tumour growth in mammals. They can be employed in this context not only in combination with other cytostatics to overcome so-called "drug resistance" or "multidrug resistance". Rather, because of their antineoplastic properties, they are suitable per se for treatment even of tumours which are regarded as therapy-resistant.

The compounds of the formula I and their salts differ in a surprising and advantageous manner from known cancer chemotherapeutics in their excellent activity, which manifests itself in a selective, controlled inhibition of proliferation and which is coupled with a low toxicity, a good bioavailability and the absence of undesirable side effects. Although the compounds of the formula I and their salts have only a slight calcium channel-blocking action, they have the pronounced ability to inhibit the growth of tumour cells in vitro, from which a corresponding in vivo action can be concluded.

The low calcium channel-blocking activity of compounds of the formula I manifests itself in the comparatively low influence of these compounds on the cardiovascular system, e.g. on blood pressure and heart rate. This weak cardiovascular activity of compounds of the formula I and their salts enables them to be used in human medicine as potent agents for inhibition of tumour growth and prevention of the formation of metastases, since they can be administered in therapeutically active doses without the risk of undesirable side effects on the cardiovascular system.

The excellent activity of compounds of the formula I and their salts enables them to be used in human medicine as chemotherapeutics for the treatment of tumours, e.g. of ovarian carcinomas, testicular tumours, prostate carcinomas, bladder tumours, oesophageal carcinomas and other malignant neoplasms, in particular intestinal cancer, breast cancer, bronchial carcinomas and pulmonary carcinomas.

In the same way as the compounds according to the invention can overcome the "drug resistance" of tumour cells, the resistance to certain malaria agents, such as e.g. chloroquine, can also be eliminated by the compounds according to the invention.

The invention therefore furthermore relates to a method for the treatment of mammals, in particular humans, suffering from one of the diseases mentioned. The method is characterized in that a therapeutically active and pharmacologically tolerated amount of one or more compounds of the formula I and/or their pharmacologically tolerated salts is administered to the sick individual.

The invention moreover relates to the compounds of the formula I and their pharmacologically tolerated salts for use in the treatment of the diseases mentioned.

The invention likewise relates to the use of compounds of the formula I and their pharmacologically tolerated salts in the preparation of medicaments which are employed for combating the diseases mentioned.

The invention furthermore relates to medicaments which contain one or more compounds of the general formula I and/or their pharmacologically tolerated salts.

The medicaments are prepared by processes which are known per se and are familiar to the expert. The pharmacologically active compounds of the formula I and their salts (=active compounds) are employed as medicaments either as such or, preferably, in combination with suitable pharmaceutical auxiliaries, in the form of tablets, coated tablets, capsules, suppositories, plasters (for transdermal drug administration), emulsions, suspensions, aerosols, sprays, ointments, creams, gels or solutions, the active compound content advantageously being between 0.1 and 95%.

The expert is familiarly, on the basis of his expert knowledge, with the auxiliaries which are suitable for the desired medicament formulations. In addition to solvents, gel-forming agents, suppository bases, tabletting auxiliaries and other active compound excipients, it is possible to use, for example, antioxidants, dispersing agents, emulsifiers, foam suppressants, flavour correctants, preservatives, solubilizing agents, dyestuffs or, in particular, permeation promoters and complexing agents (e.g. cyclodextrins).

The active compounds can be administered rectally, by inhalation, parenterally (perlingually, intravenously or percutaneously) or orally.

In general, it has proved advantageous in human medicine to administer the active compound or compounds, in the case of oral administration, in a daily dose of about 0.5 to 30 mg/kg of body weight, if desired in the form of several, preferably 1 to 4, individual doses, in order to achieve the desired result. For a parenteral treatment, similar or (in particular for intravenous administration of the active compounds) as a rule lower dosages can be used.

The particular optimum dosage and mode of administration required for the active compounds can easily be specified by any expert on the basis of his expert knowledge.

If the compounds according to the invention and/or their pharmacologically tolerated salts are to be employed for the treatment of the diseases mentioned, the pharmaceutical formations can also contain one or more other pharmacologically active constituents of other groups of medicaments.

As is customary in internal tumour therapy, treatment with the medicaments according to the invention can be combined with administration of other cytostatics having different action spectra, to reduce the risk of side effects. It may also be advantageous to carry out the treatment in accordance with the principle of cyclic cytostatic therapy. In this case, each treatment is separated by a recovery phase. This utilizes the finding that healthy tissue of most organs regenerates faster than malignant tissue.

Measurement of the Inhibition of Proliferation

The particular cell suspension—ZR-75 or amnion—(50,000 cells/ml in RIMEN+10% FCS+insulin) is incubated in culture dishes for 24 h in an incubation cabinet. After this time, the cells have grown, and the medium is sucked off and replaced by new medium without (control) or with test substance. The medium used to measure the substance effects (RIMEN) contains 2% oestrogen-free FCS (oestrogen-free by dextran/active charcoal treatment) and no insulin. The cell lines are treated with test substance for in each case 6 days. After 72 h, the medium is replaced. After incubation with the substance for 6 days, the cell growth is quantified by determination of the DNA content by the BURTON method (J. Steroid Biochem. 20, 1083–1088, 1984).

The compound 5-acetyl-2,6-dimethyl-3-[5-(4,4-diphenyl-1-piperidinyl)-pentanoyl]-4-(3-nitrophenyl)-pyridine fumarate inhibits cell proliferation with an $IC_{50}$ value of 0.8 $\mu M$ (ZR-75) or >5 $\mu M$ (amnion).

The compound 5-acetyl-4-(2,3-dichlorophenyl)-2,6-dimethyl-3-[5-(4,4-diphenyl-1-piperidinyl)pentanoyl]-pyridine fumarate inhibits cell proliferation with an $IC_{50}$ value of 0.38 $\mu M$ (ZR-75) or 1.2 $\mu M$ (amnion).

We claim:

1. A pyridine compound of formula I

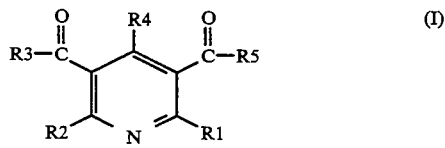

wherein
one of the radicals R1 and R5 denotes 1–6C-alkyl and the other denotes the grouping -E1-E2-N(R6a)R6b
R2 denotes hydrogen, 1–6C-alkyl or, together with R3, 2–3C-alkylene,
R3 denotes 1–4C-alkyl, 1–4C-alkoxy, 3–5C-alkoxyalkyl, 3–5C-alkoxyalkoxy or, together with R2, 2–3C-alkylene,
R4 denotes phenyl which is substituted by R41 and R42,
R41 denotes hydrogen, hydroxyl, halogen, nitro, cyano, trifluoromethyl, 1–4C -alkyl, 1–4C-alkoxy, 1–4C-alkoxy which is completely or partly substituted by fluorine, 1–4C-alkoxycarbonyl, 2–5C-acyl, amino or mono- or di-1–4—C-alkylamino,
R42 denotes hydrogen, hydroxyl, halogen, nitro, cyano, trifluoromethyl, 1–4C-alkyl, 1–4C-alkoxy, 1–4C-alkoxy which is completely or partly substituted by fluorine, 1–4C-alkoxycarbonyl, 2–5C-acyl; amino or mono-or di-1–4C-alkylamino, E1 denotes methylene (CH₂), E2 denotes straight-chain or branched 1–7C-alkylene, the grouping -(CH₂)$_m$-E-(CH₂)$_n$-or the grouping -A1-O-A2-, E denotes vinylene (—CH=CH—) or ethinylene (—C≡C-), m denotes the number 1 or 2, n denotes the number 1 or 2, A1 denotes a bond or 2–4C-alkylene, A2 denotes 2–4C-alkylene or 2C-alkylenoxy-2C-alkylene, R6a l and R6b, together and including the nitrogen atom to which they are both bonded, represent a radical of the formula

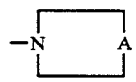

wherein

A denotes —CH₂—CH₂C(R7)R8—CH₂—CH₂-, —CH₂—CH₂CHR9—CH₂—CH₂- or —CH₂—CH₂—CH₂—CHR10-, R7 denotes hydrogen (H) or aryl and R8 denotes aryl, or R7 and R8 together denote diarylmethylene, R9 denotes diaryl-1–4C-alkyl and R10 denotes aryl-1–4C-alkyl, wherein aryl represent a ring of the formula

wherein R11 and R12 are identical or different and denote hydrogen (H), 1–4C-alkyl, 1–4C-alkoxy, halogen, hydroxyl, trifluoromethyl or, together, methylenedioxy, or salt thereof.

2. A compound of formula I according to claim 1, wherein

E2 denotes straight-chain or branched 1–5C-alkylene, the grouping -(CH₂$_m$-E-(CH₂)$_n$- or the grouping -A1-O-A2- and A1 denotes 2–4C-alkylene, or a salt thereof.

3. A compound of claim 1 of formula Ia

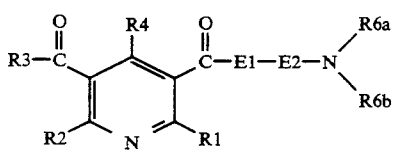

wherein

R1 denotes 1–6C-alkyl and R2, R3, R4, E1, E2, R6a and R6b have the meanings given in claim 1, or a salt thereof.

4. A compound of claim 1 of formula Ib

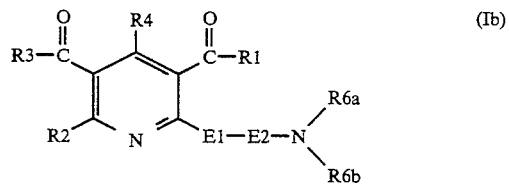

wherein

R1 denotes 1–6C-alkyl and R2, R3, R4, E1, E2, R6a and R6b have the meanings given in claim 1, or a salt thereof.

5. A compound of formula I according to claim 1, in which one of the radicals R1 and R5 denotes 1–6C-alkyl and the other denotes the grouping -E1-E2-n(R6a)R6b, R2 denotes 1–4C-alkyl or, together with R3, 2–3C-alkylene, R3 denotes 12–4C-alkyl, branched-chain 3–4C-alkoxy or, together with R2, 2–3C-alkylene, R4 denotes phenyl which is substituted by R41 and R42, R41 denotes hydrogen, chlorine or nitro, R42 hydrogen or chlorine, E1 denotes methylene (CH₂), E2 denotes ethylene, propylene, tetramethylene, pentamethylene, hexamethylene or the grouping -A1l-O-A2-, A1 denotes a bond, A2 denotes ethylene, R6a and R6b, together and including the nitrogen atom to which they are both bonded, represent a radical of the formula

wherein

A denotes —CH₂—CH₂—C(R7(R8—CH₂—CH₂-, —CH₂—CH₂—CHR9—CH₂—CH₂- or —CH₂—CH₂—CH₂—CHR10, R7 denotes hydrogen or phenyl and R8 denotes phenyl, or R7 and R8 together denote diphenylmethylene, R9 denotes diphenylmethylene (benzhydryl) and R10 denotes benzyl or 4-chlorobenzyl, or a salt thereof.

6. A compound of formula I according to claim 1, in which one of the radicals R1 and R5 denotes 1–4C-alkyl and the other denotes the grouping -E1-E2-N(R6a)R6b, R2 denotes 1–4C-alkyl or, together with R3, 2–3C-alkylene, R3 denotes 1–4C-alkyl, branched-chain 3–4C-alkoxy or, together with R2, 2–3C-alkylene, R4 denotes 3-nitrophenyl or 2,3-dichlorophenyl, E1 denotes methylene, E2 denotes propylene, tetramethylene, pentamethylene, hexamethylene or the grouping -A1-O-A2, A1 denotes a bond, A2 denotes ethylene, R6a and R6b, together and including the nitrogen atom to which they are both bonded, represent a radical of the formula

wherein
A denotes —CH₂—CH₂—C(R7(R8—CH₂—CH₂-,
R7 denotes phenyl an
R8 denotes phenyl, or
R7 and R8 together denote diphenylmethylene, or a salt thereof.

7. A compound of formula I according to claim 1, in which one of the radicals R1 and R5 denotes 1–4C-alkyl and the other denotes the grouping -E1-E2-N(R6*a*)R6*b*,
R2 denotes 1–4C-alkyl,
R3 denotes 1–4C-alkyl or branched chain 3–4C-alkoxy,
R4 denotes 3-nitrophenyl,
R1 denotes methylene,
E2 denotes ethylene or propylene, R6*a* and R6*b*, together and including the nitrogen atom to which they are both bonded, represent a radical of the formula

wherein
A denotes —CH₂—CH₂—C(R7)R8—CH₂—CH₂-,
R7 denotes phenyl and
R8 denotes phenyl, or a salt thereof.

8. A medicament composition containing a suitable carrier and an effective amount of one or more compounds according to claim 1, or a pharmacologically tolerated salt thereof.

* * * * *

UNITED STATES PATENT AND TRADEMARK OFFICE
CERTIFICATE OF CORRECTION

PATENT NO. : 5,352,684

DATED : October 4, 1994

INVENTOR(S) : Peter Zimmerman, Wolf-Rudiger Ulrich

It is certified that error appears in the above-indentified patent and that said Letters Patent is hereby corrected as shown below:

Column 1, line 61, "E2 straight-chain" should read --E2 denotes straight chain--; line 65, "(-CaC-)" should read --(-C≡C-). Column 2, line 58, "is" should read --in--; after line 63, start new paragraph and insert --1-4C Alkoxycarbonyl contains, in addition to the carbonyl group, one of the abovementioned 1-4C alkoxy radicals.--. Column 3, line 9, "$CH_2$-9 ,"  should read --$CH_2$-],--; line 10, "isopropylene" should read --isopropylidene--; line 11, "$CH_2$-·" should read --$CH_2$-]--; line 16, "(-$CH_2$-$CH_2$-," should read --(-$CH_2$-$CH_2$-),--; line 22, "-$CH_2$-" should read -- -(-$CH_2$-$CH_2$- --; line 25 "radicals" should read --radicals:--; line 38, "difluorobenzyl" should read --difluorobenzhydryl--; line 39, "dimethylbenzhydryl" should read --dimethoxybenzhydryl--; line 41, "Aryl-1-41 C-alkyl" should read --Aryl-1-4C-alkyl--; line 50, "which" should read --acids which--; line 58, "know" should read --known--; line 62 "bibenzate" should read --hibenzate--. Column 4, line 41, "R2" should read --E2--; line 43, "-A1O-A2," should read -- -A1-O-A2-,--; line 67, "R1" should read --E1--; line 68, "A2R6a," should read --A2, R6a,--. Column 5, line 10, "3-3-C-alkylene" should read --2-3C-alkylene--. Column 19, line 24, "R4E1" should read --R4, E1--. Column 21, line 18, "mol" should read --ml--; line 24, delete "2-(1,4-dihydro-"; line 43, "After acetate" should read --After 10 min, 30 ml water are added. The mixture thus obtained is extracted with ethyl acetate.--; line 54, "ethoxy)-" should read --ethoxy]- --; line 55, "methyl-4" should read --methyl-6-methyl-4--; line 64, "3-[60" should read --3-[6- --. Column 22, line 10, "235°237.5°" should read --235-237.5°; line 25, "obtained, 5 ml is" should read --obtained which is dissolved in 12 ml isopropanol, and 0.15 g (1.3 mmol) fumaric acid in 5 ml--; line 30, "3-(chloropen-" should read --3-(5-chloropen- --; line 31, "tanoyl)4" should read --tanoyl)-4--; line 64, "c" should read --C--.

UNITED STATES PATENT AND TRADEMARK OFFICE
CERTIFICATE OF CORRECTION

PATENT NO. : 5,352,684
DATED : October 4, 1994
INVENTOR(S) : Peter Zimmerman, Wolf-Rudiger Ulrich It is certified that error appears in the above-indentified patent and that said Letters Patent is hereby corrected as shown below:

Column 23, line 23, "2-([4-" should read --2-[4- --; line 24, "-6methyl" should read-- -6-methyl--;
line 38, "230 ≥" should read --230--; line 43, delete "2,6-dimethyl-" (second ocurrence); line 58, "1-5," should read --1-chloro-5,--. Column 24, line 9, "bromohexanyol)4" should read --bromohexanyol)-4--; line 31, "-2[4-" should read --2-[4- --; line 32, "-4(2,3-dichloro-" should read -- -4-(2,3-dichloro- --; line 55, "8/2The" should read --8/2. The--. Column 25, line 31, "ethyl" should read --ethoxy--; line 42, "methoxy" should read --methyl--. Column 27, line 40, "familiarly" should read --familiar--. Column 28, line 40, delete "compound". Column 29, line 14, delete "1". Column 30, line 16, "n" should read--N--; line 28, "-All-" should read -- -Al- --; line 42, "(R7(R8" should read --(R7)R8--. Column 31, line 8, "C(R7(R8" should read C(R7)R8--.

Signed and Sealed this

Twenty-fifth Day of April, 1995

BRUCE LEHMAN

Attest:

Attesting Officer

Commissioner of Patents and Trademarks